United States Patent
Watanabe et al.

(10) Patent No.: US 11,603,563 B2
(45) Date of Patent: Mar. 14, 2023

(54) METHOD OF PREDICTING DIFFERENTIATION POTENTIAL OF IPS CELLS INTO CARTILAGE CELLS BASED ON GENE EXPRESSION PROFILES

(71) Applicants: Shimadzu Corporation, Kyoto (JP); Kyoto University, Kyoto (JP)

(72) Inventors: Makoto Watanabe, Kyoto (JP); Taka-Aki Sato, Kyoto (JP); Junya Toguchida, Kyoto (JP)

(73) Assignees: Shimadzu Corporation, Kyoto (JP); Kyoto University, Kyoto (JP)

( * ) Notice: Subject to any disclaimer, the term of this patent is extended or adjusted under 35 U.S.C. 154(b) by 98 days.

(21) Appl. No.: 16/620,647

(22) PCT Filed: Jun. 8, 2018

(86) PCT No.: PCT/JP2018/022116
§ 371 (c)(1),
(2) Date: Dec. 9, 2019

(87) PCT Pub. No.: WO2018/225868
PCT Pub. Date: Dec. 13, 2018

(65) Prior Publication Data
US 2020/0140946 A1    May 7, 2020

(30) Foreign Application Priority Data
Jun. 10, 2017    (JP) .............................. JP2017-114804

(51) Int. Cl.
*C12Q 1/68* (2018.01)
*C12Q 1/6876* (2018.01)

(52) U.S. Cl.
CPC ..... *C12Q 1/6876* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 9,921,212 B2 | 3/2018 | Toguchida et al. | |
| 2013/0296183 A1* | 11/2013 | Eggan | A61P 25/00 506/9 |
| 2016/0177406 A1 | 6/2016 | Toguchida et al. | |

FOREIGN PATENT DOCUMENTS

| | | | |
|---|---|---|---|
| JP | 2013-545439 A | 12/2013 | |
| JP | 2016-088909 A | 5/2016 | |
| WO | 2012/037456 A1 | 3/2012 | |

OTHER PUBLICATIONS

Office Action issued in counterpart Japanese Patent Application No. 2019-523997 dated Sep. 14, 2021.
International Search Report issued in corresponding International Patent Application No. PCT/JP2018/022116 dated Sep. 4, 2018.
Written Opinion issued in corresponding International Patent Application No. PCT/JP2018/022116 dated Sep. 4, 2018.
Umeda et al., "Long-Term Expandable SOX9+ Chondrogenic Ectomesenchymal Cells from Human Pluripotent Stem Cells," Stem Cell Reports, 4: 712-726 (2015).
Fukuta et al., "Derivation of Mesenchymal Stromal Cells from Pluripotent Stem Cells through a Neural Crest Lineage using Small Molecule Compounds with Defined Media," PLOS One, 9(12): e112291 (2014).
"*Homo sapiens* zinc finger protein 91 pseudogene (LOC441666), non-coding RNA," NCBI Reference Sequence: NR_024380.1 [online] National Center for Biotechnology Information [https://www.ncbi.nlm.nih.gov/nuccore/211971053?sat=46&satkey=135779184] (2017).
Decision of Refusal issued in related Japanese Patent Application No. 2019-523997 dated Apr. 7, 2022.
Decision of Dismissal of Amendment issued in related Japanese Patent Application No. 2019-523997 dated Apr. 7, 2022.

* cited by examiner

*Primary Examiner* — Juliet C Switzer
(74) *Attorney, Agent, or Firm* — Morgan, Lewis & Bockius LLP (57) ABSTRACT

Provided is a method of predicting differentiation potential of undifferentiated iPS cells into cartilage cells. Provided is a genetic marker for predicting differentiation potential of undifferentiated iPS cells into cartilage cells. A method of predicting differentiation potential of undifferentiated iPS cells into cartilage cells based on gene expression data of the undifferentiated iPS cells. A method of predicting differentiation potential of undifferentiated iPS cells into cartilage cells by predicting differentiation potential of the iPS cells into neural crest cells (NC cells) based on gene expression data of the undifferentiated iPS cells.

9 Claims, 12 Drawing Sheets

METHOD OF PREDICTING DIFFERENTIATION POTENTIAL OF IPS CELLS INTO CARTILAGE CELLS BASED ON GENE EXPRESSION PROFILES

TECHNICAL FIELD

The present invention belongs to the fields of regenerative medicine, cell culture, and basic research for both fields, and it relates to a method of predicting differentiation potential of undifferentiated iPS cells into cartilage cells. The present invention also relates to a genetic marker for predicting differentiation potential of undifferentiated iPS cells into cartilage cells. The present invention can be utilized by a user in the fields of regenerative medicine, cell culture, and basic research for both fields who is in need of generating cartilage cells from iPS cells.

BACKGROUND ART

Recently, mouse and human induced pluripotent stem cells (iPS cells) have been established. Differentiation potential of iPS cells into cartilage cells varies with cell lines.

Figure 1:
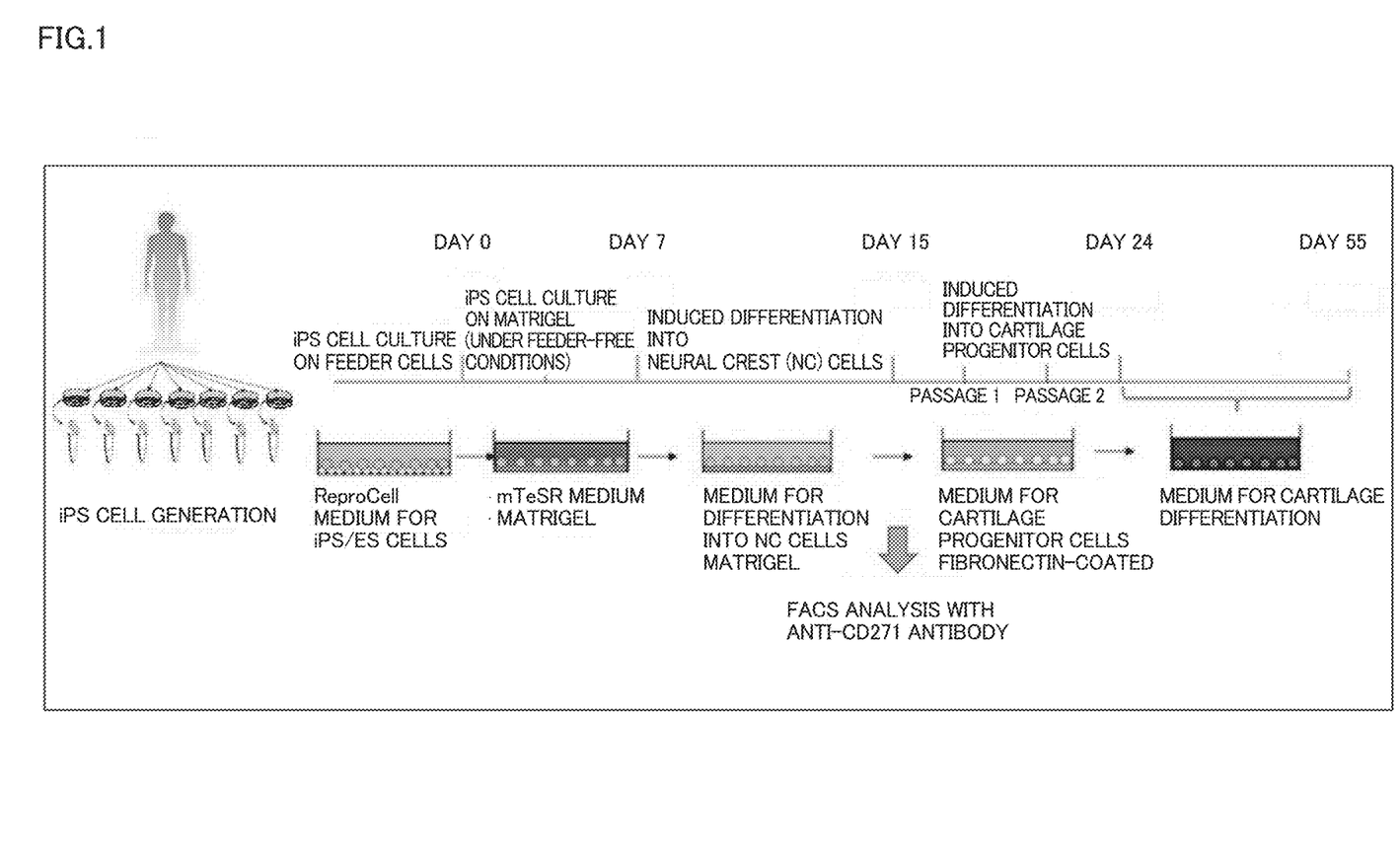
FIG. 1 schematically illustrates a pathway that involves induced differentiation of iPS cells into cartilage cells.

Generation of cartilage cells from iPS cells can be achieved by using a pathway that involves induced differentiation of iPS cells into neural crest cells (NC cells) and then into cartilage cells (FIG. 1). FIG. 1 schematically illustrates a pathway that involves induced differentiation of iPS cells into cartilage cells. Referring to FIG. 1, iPS cells are cultured on feeder cells (the day of completion of this culture is defined as Day 0) and then cultured on Matrigel (under feeder-free conditions) (this culture completes on about Day 7, for example); the cultured undifferentiated iPS cells are induced to differentiate into NC cells (this culture completes on about Day 15, for example); the resulting NC cells are further induced to differentiate into cartilage progenitor cells on cartilage progenitor cell medium (fibronectin-coated) (via passage 1 and passage 2; this culture completes on about Day 24, for example); and the resulting cartilage progenitor cells are induced into cartilage cells on cartilage differentiation medium (this culture completes on about Day 55, for example).

Figure 2:
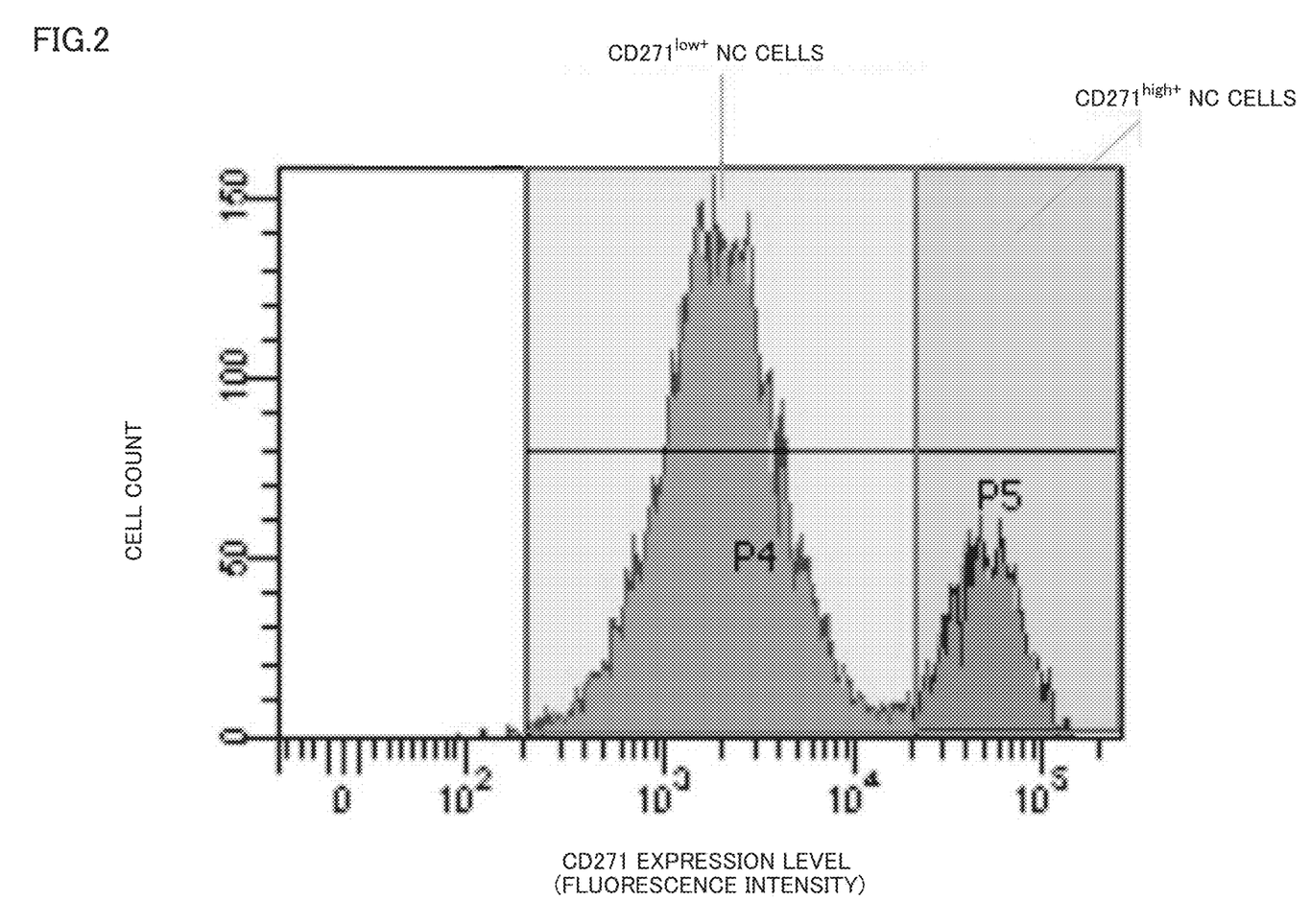
FIG. 2 shows an expression level of NC marker CD271 in neural crest cells (NC cells), with the abscissa representing CD271 expression level (fluorescence intensity) and the ordinate representing cell count.

After differentiation of iPS cells into NC cells, analysis is performed by using anti-CD271 antibody (where CD271 is a cell surface marker protein of NC cells) and using fluorescence flow cytometry (FACS). Based on the analysis, the NC cells are divided into an NC cell population with low CD271 expression level ($CD271^{low+}$ NC cells) and an NC cell population with high CD271 expression level ($CD271^{high+}$ NC cells) (FIG. 2). FIG. 2 shows the expression level of NC marker CD271 in neural crest cells (NC cells), with the abscissa representing CD271 expression level (fluorescence intensity) and the ordinate representing cell count. In FIG. 2, the NC cell population with low CD271 expression level ($CD271^{low+}$ NC cells) is named P4 fraction and the NC cell population with high CD271 expression level ($CD271^{high+}$ NC cells) is named P5 fraction.

According to reports, when such NC cells are further induced to differentiate into cartilage cells, cartilage cells differentiated from the $CD271^{high+}$ NC cell population have higher expression levels of cartilage-related genes than cartilage cells differentiated from the $CD271^{low+}$ NC cell population (NPLs 1, 2). Therefore, a user can use the CD271 expression level of NC cells derived from induced differentiation of iPS cells as an index for selecting an iPS cell line with a high proportion of $CD271^{high+}$ NC cells (high differentiation potential). This procedure allows the user to select iPS cells with high differentiation potential into cartilage.

See Japanese Patent Laying-Open No. 2016-88909 and the like for the method of inducing differentiation of iPS cells into neural crest cells (NC cells) and the method of inducing differentiation of neural crest cells (NC cells) into cartilage progenitor cells and further into cartilage cells.

CITATION LIST

Patent Literature

PTL 1: Japanese Patent Laying-Open No. 2016-88909

Non Patent Literature

NPL 1: Umeda K. et al., Long-Term Expandable SOX9+ Chondrogenic Ectomesenchymal Cells from Human Pluripotent Stem Cells, Stem Cell Reports. 2015 Apr. 14; 4(4):712-726

NPL 2: Fukuta M. et al., Derivation of Mesenchymal Stromal Cells from Pluripotent Stem Cells through a Neural Crest Lineage using Small Molecule Compounds with Defined Media, PLoS One. 2014 2; 9(12)

SUMMARY OF INVENTION

Technical Problem

Differentiation potential of iPS cells into cartilage cells varies with cell lines. For this reason, a user attempting to generate cartilage cells from iPS cells needs to select iPS cells with high differentiation potential into cartilage cells. In order to sort the total population of generated iPS cell lines to select iPS cell lines with high differentiation potential into cartilage cells, one can analyze the cartilage cells derived from induced differentiation of the iPS cells and then use as an index the results of cartilage gene expression and/or immunohistochemical staining, for example. An alternative means that has been employed is, as described above, FACS analysis of NC cells derived from induced differentiation of iPS cells and use of the value of the proportion of the $CD271^{high+}$ NC cell population as an index.

At this point, however, there is no marker or technique that can be used to predict the differentiation potential of undifferentiated iPS cells. If available, prediction of differentiation potential of undifferentiated iPS cells is a very useful tool in the fields of regenerative medicine and basic research because it does not require induced differentiation of a low-differentiation-potential iPS cell line into NC cells and further into cartilage cells and, thereby, it enables efficient cell culture and running cost reduction.

An object of the present invention is to provide a method of predicting differentiation potential of undifferentiated iPS cells into cartilage cells. Another object of the present invention is to provide a genetic marker for predicting differentiation potential of undifferentiated iPS cells into cartilage cells.

Solution to Problem

The inventors of the present invention have conducted intensive research and, as a result, have found that differentiation potential of undifferentiated iPS cells into cartilage cells is predictable based on gene expression data of the undifferentiated iPS cells.

The present invention includes the invention described below.

(1) A method of predicting differentiation potential of undifferentiated iPS cells into cartilage cells based on gene expression data of the undifferentiated iPS cells.

(2) A method of predicting differentiation potential of undifferentiated iPS cells into cartilage cells by predicting differentiation potential of the iPS cells into neural crest cells (NC cells) based on gene expression data of the undifferentiated iPS cells.

(3) The method according to (1) or (2) above, wherein gene expression profile data of target undifferentiated iPS cells is obtained and an expression level of a particular gene is obtained, an expression level ratio which is a ratio of the expression level of the particular gene to an expression level of the same gene in reference undifferentiated iPS cells with low differentiation potential (control) is calculated:

[Expression level ratio]=[Expression level of the particular gene in target undifferentiated iPS cells]/[Expression level of the same gene in reference undifferentiated iPS cells with low differentiation potential (control)], and when the expression level ratio thus calculated is lower than 0.9 for a gene with decreased expression or higher than 1.1 for a gene with increased expression, determination is made that the target undifferentiated iPS cells have a high differentiation potential into cartilage cells.

(4) The method according to any one of (1) to (3) above, wherein the gene with decreased expression as the particular gene is at least one selected from the group consisting of genes with gene IDs (Unique Sorted Transcript Cluster IDs) 16713399, 16984394, 17121974, 17122170, 16860191, 16999432, 17121970, 17065663, 17028547, 17022610, 17035441, 16825196, 16946689, 16906788, 16700250, 17048704, 16729023, 16938761, 16885703, 17000077, 16917881, 16809811, 16684087, 17092402, 16826158, 17038957, 16684995, 17103991, 16897399, and 16696918, and the gene with increased expression as the particular gene is at least one selected from the group consisting of genes with gene IDs 16788743, 16788693, 16788572, 17118804, 16662749, 17100659, 16747661, 17083911, 16788727, 16692589, 16729321, 16976012, 16697219, 16798158, 16990845, 17118850, 16830980, 16778675, 17110283, 16851422, 16797049, 16838105, 16831379, 16875952, 17117410, 17103230, 16999147, 16688792, 16718764, 17072022, and 16679331.

(5) A method of predicting differentiation potential of undifferentiated iPS cells into cartilage cells, wherein the predicting is performed by obtaining gene expression profile data of target undifferentiated iPS cells and obtaining an expression level of a particular gene, constructing a discrimination model, calculating a prediction score from the discrimination model and a gene profile of the particular gene, and using the prediction score for the predicting.

(6) The method according to any one of (1) to (5) above, wherein the undifferentiated iPS cells are feeder-free undifferentiated iPS cells.

(7) A method comprising:

predicting differentiation potential of undifferentiated iPS cells into cartilage cells by the method according to any one of (1) to (6) above; and as for undifferentiated iPS cells with high differentiation potential into cartilage cells in accordance with determination, inducing differentiation into cartilage cells.

(8) A genetic marker for predicting differentiation potential of undifferentiated iPS cells into cartilage cells, wherein the genetic marker is:

at least one selected from the group consisting of genes with decreased expression with gene IDs (Unique Sorted Transcript Cluster IDs) 16713399, 16984394, 17121974, 17122170, 16860191, 16999432, 17121970, 17065663, 17028547, 17022610, 17035441, 16825196, 16946689, 16906788, 16700250, 17048704, 16729023, 16938761, 16885703, 17000077, 16917881, 16809811, 16684087, 17092402, 16826158, 17038957, 16684995, 17103991, 16897399, and 16696918; or at least one selected from the group consisting of genes with increased expression with gene IDs 16788743, 16788693, 16788572, 17118804, 16662749, 17100659, 16747661, 17083911, 16788727, 16692589, 16729321, 16976012, 16697219, 16798158, 16990845, 17118850, 16830980, 16778675, 17110283, 16851422, 16797049, 16838105, 16831379, 16875952, 17117410, 17103230, 16999147, 16688792, 16718764, 17072022, and 16679331.

Advantageous Effects of Invention

The present invention provides a method of predicting differentiation potential of undifferentiated iPS cells into cartilage cells.

Differentiation potential of iPS cells into cartilage cells varies with cell lines. For this reason, a user attempting to generate cartilage cells from iPS cells needs to select iPS cells with high differentiation potential into cartilage cells. Conventionally, however, there is no marker or technique that can be used for predicting differentiation potential of undifferentiated iPS cells. According to the present invention, differentiation potential of undifferentiated iPS cells into cartilage cells can be predicted and, also, discrimination between an undifferentiated iPS cell line with high differentiation potential into cartilage cells and an undifferentiated iPS cell line with low differentiation potential into cartilage cells can be performed without requiring induced differentiation of the iPS cell lines into NC cells and further into cartilage cells. Thereby, an iPS cell line with high differentiation potential into cartilage cells can be selected and used for efficient induction of differentiation into cartilage cells. Thus, the present invention is very useful in the fields of regenerative medicine and basic research. Furthermore, according to the present invention, score-based prediction (scoring) of whether iPS cells have a good differentiation potential (whether the proportion of $CD271^{high+}$ NC cells is higher than 20%, for example) can be provided based on an expression level of a particular gene. Therefore, by application of the present invention to other iPS cell lines with unknown differentiation potential, one can predict differentiation potential of these iPS cells into cartilage cells.

The present invention also provides a genetic marker for predicting differentiation potential of undifferentiated iPS cells into cartilage cells.

DESCRIPTION OF EMBODIMENTS

The present invention provides a method of predicting differentiation potential of undifferentiated iPS cells into cartilage cells based on gene expression data of the undifferentiated iPS cells. In the following, a description will be given.

Figure 3:
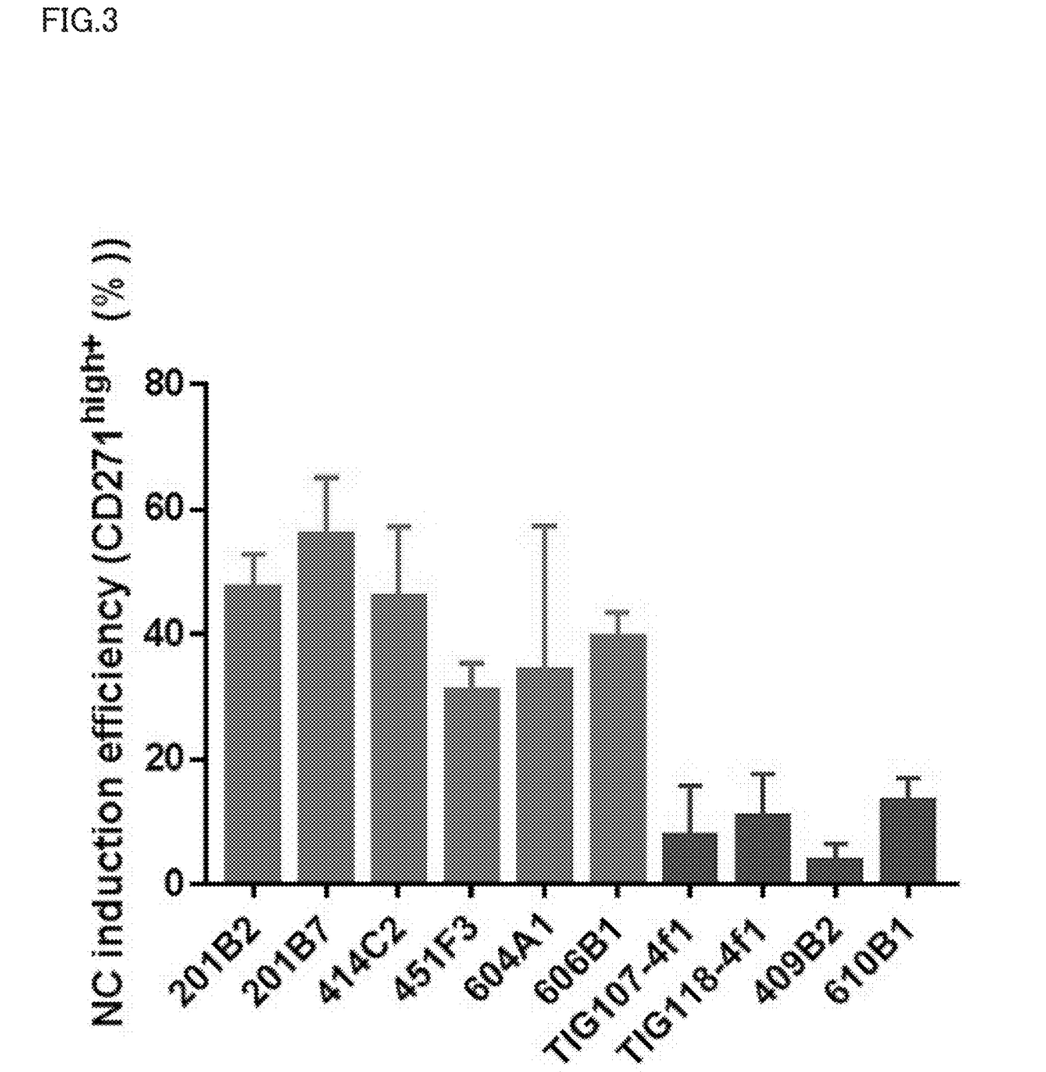
FIG. 3 shows differentiation efficiency of iPS cell lines into neural crest cells (NC cells) [NC induction efficiency (CD271$^{high+}$ (%))].

Each of ten undifferentiated iPS cell lines (201B2, 201B7, 414C2, 409B2, TIG118-4f1, 604A1, 606A1, 610B1, 451F3, TIG107-4f1) was induced to differentiate into neural crest cells (NC cells). The differentiated NC cells were subjected to reaction with anti-CD271 antibody to obtain a sample (cells), and the resulting sample was analyzed by fluorescence flow cytometry (FACS). The proportion of CD271$^{high+}$ NC cells was calculated for use as NC differentiation efficiency. FIG. 3 shows differentiation efficiency of iPS cell lines into neural crest cells (NC cells) [NC induction efficiency (CD271$^{high+}$ (%))]. The ordinate represents the proportion of CD271$^{high+}$ NC cells in the total NC cells. As shown in FIG. 3, the NC cells were divided into cell groups with high differentiation efficiency into NC cells (six cell lines 201B2, 201B7, 414C2, 451F3, 604A1, 606B1) and cell groups with low differentiation efficiency into NC cells (four cell lines 409B2, 610B1, TIG118-4f1, TIG107-4f1).

Figure 4:
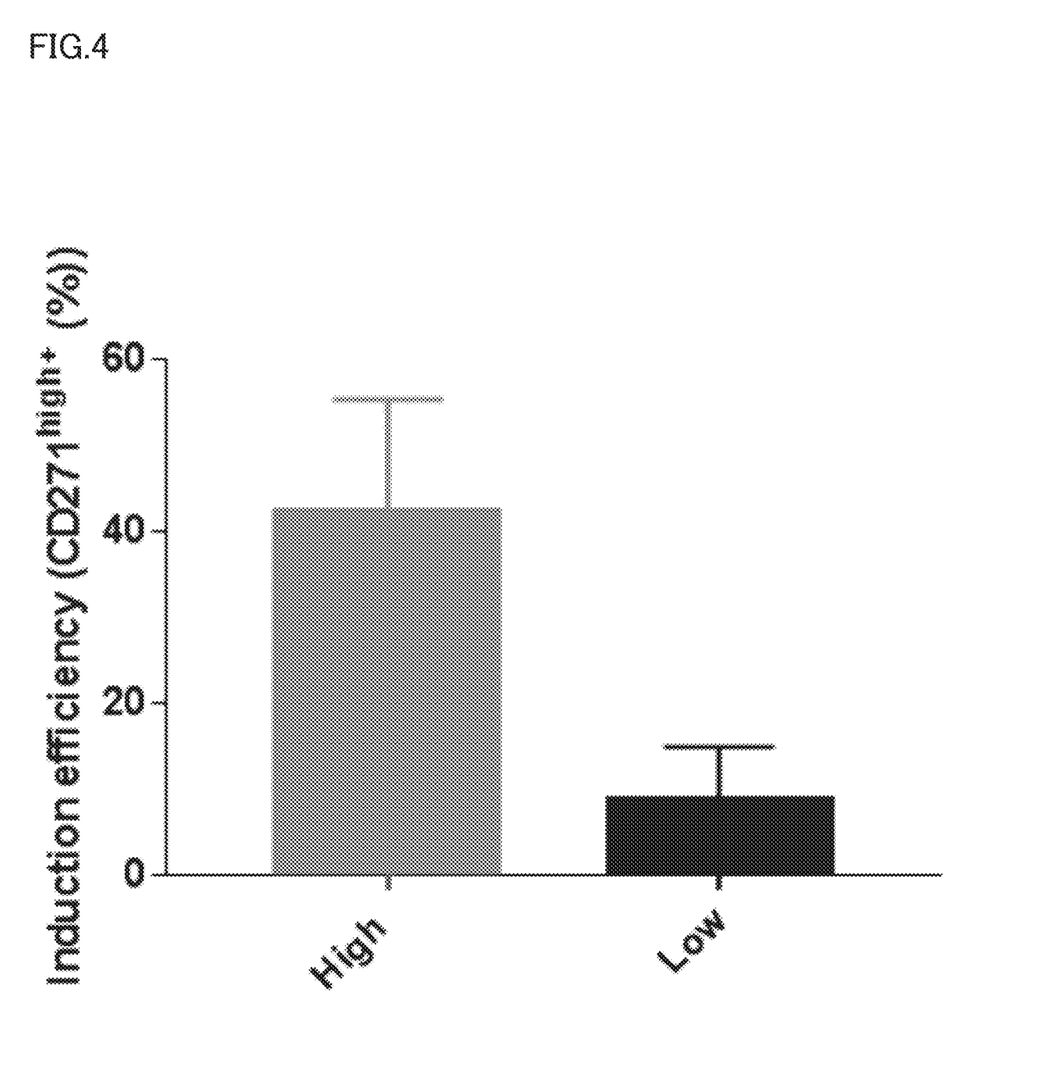
FIG. 4 shows t-test comparison between differentiation efficiency of cell groups with high differentiation efficiency into neural crest cells (NC cells) (High) and differentiation efficiency of cell groups with low differentiation efficiency into neural crest cells (NC cells) (Low) [Induction efficiency (CD271$^{high+}$ (%))].

Then, comparative analysis of differentiation efficiency of the cell groups with high differentiation efficiency (six cell lines 201B2, 201B7, 414C2, 451F3, 604A1, 606B1) and differentiation efficiency of the cell groups with low differentiation efficiency (four cell lines 409B2, 610B1, TIG118-4f1, TIG107-4f1) was carried out by t-test, and results revealed a statistically significant difference (p<0.001) in differentiation efficiency (FIG. 4). FIG. 4 shows t-test comparison between differentiation efficiency of the cell groups with high differentiation efficiency into neural crest cells (NC cells) (High) and differentiation efficiency of the cell groups with low differentiation efficiency into neural crest cells (NC cells) (Low) [Induction efficiency (CD271$^{high+}$ (%))].

Referring to results shown in FIGS. 3 and 4, a high differentiation efficiency into neural crest cells (NC cells) corresponds to a proportion of CD271$^{high+}$ NC cells in the total neural crest cells (NC cells) that is equal to or higher than 15%, equal to or higher than 18%, equal to or higher than 20%, equal to or higher than 25%, or equal to or higher than 30%, for example.

Then, RNA was extracted from the iPS cells and GeneChip® Human Gene 2.0 ST Array (manufactured by Thermo Fisher SCIENTIFIC) was used to obtain gene expression profiles (of all the 48145 genes). Among the resulting gene profiles, gene profiles of the groups with high differentiation efficiency into neural crest cells (NC cells) and gene profiles of the groups with low differentiation efficiency into neural crest cells (NC cells) (control) were compared. According to the comparison, 61 genes showed a change by a factor of 1.5 times or more, which was statistically significant (p<0.05 in t-test significance testing). More specifically, the ratio of the average expression level of a particular gene in the cell groups with high differentiation efficiency into NC cells (six cell lines 201B2, 201B7, 414C2, 451F3, 604A1, 606B1) to the average expression level of the same gene in the cell groups with low differentiation efficiency into NC cells (four cell lines 409B2, 610B1, TIG118-4f1, TIG107-4f1):

[Expression level ratio]=[Expression level of the particular gene in groups with high efficiency]/[Expression level of the same gene in groups with low efficiency]

was calculated, and, according to the results, 61 genes showed a change by a factor of 1.5 times or more (in terms of Fold Change (the amount of change in expression) defined below), which was statistically significant (p<0.05 in t-test significance testing).

The 61 genes consist of:

30 genes with decreased expression with gene IDs (Unique Sorted Transcript Cluster IDs) 16713399, 16984394, 17121974, 17122170, 16860191, 16999432, 17121970, 17065663, 17028547, 17022610, 17035441, 16825196, 16946689, 16906788, 16700250, 17048704, 16729023, 16938761, 16885703, 17000077, 16917881, 16809811, 16684087, 17092402, 16826158, 17038957, 16684995, 17103991, 16897399, and 16696918 (Table 1); and 31 genes with increased expression with gene IDs 16788743, 16788693, 16788572, 17118804, 16662749, 17100659, 16747661, 17083911, 16788727, 16692589, 16729321, 16976012, 16697219, 16798158, 16990845, 17118850, 16830980, 16778675, 17110283, 16851422, 16797049, 16838105, 16831379, 16875952, 17117410, 17103230, 16999147, 16688792, 16718764, 17072022, and 16679331 (Table 2).

Table 1 lists groups of genes the expression of which is decreased in the cell groups with high differentiation efficiency into NC cells. The Fold Change (the amount of change in expression) of a gene with decreased expression is expressed as the reciprocal of the [Expression level ratio]

obtained by the above equation with a minus sign. More specifically, the smaller the Fold Change (the amount of change in expression), the smaller the average expression level of the particular gene in the cell groups with high differentiation efficiency into NC cells (201B2, 201B7, 414C2, 451F3, 604A1, 606B1) relative to the average expression level of the same gene in the cell groups with low differentiation efficiency into NC cells (409B2, 610B1, TIG118-4f1, TIG107-4f1).

Table 2 lists groups of genes the expression of which is increased in the cell groups with high differentiation efficiency into NC cells. The Fold Change (the amount of change in expression) of a gene with increased expression is expressed as the [Expression level ratio] obtained by the above equation. More specifically, the greater the Fold Change (the amount of change in expression), the greater the average expression level of the particular gene in the cell groups with high differentiation efficiency into NC cells (201B2, 201B7, 414C2, 451F3, 604A1, 606B1) relative to the average expression level of the same gene in the cell groups with low differentiation efficiency into NC cells (409B2, 610B1, TIG118-4f1, TIG107-4f1).

TABLE 1

Groups of genes the expression of which is decreased in cell groups with high differentiation efficiency

| Unique Sorted Transcript ClusterID | gene symbol | Fold Change | p-value |
| --- | --- | --- | --- |
| 16713399 | LOC441666\|RP11-313J2.1 | −4.896112 | 0.0478233 |
| 16984394 | CCDC152 | −3.664552 | 0.041689 |

TABLE 1-continued

Groups of genes the expression of which is decreased in cell groups with high differentiation efficiency

| Unique Sorted Transcript ClusterID | gene symbol | Fold Change | p-value |
| --- | --- | --- | --- |
| 17121974 | LINC00664 | −2.983343 | 0.0254418 |
| 17122170 | LINC00664 | −2.605347 | 0.0348424 |
| 16860191 | LINC00664 | −2.091242 | 0.0461873 |
| 16999432 | C5orf63 | −2.026415 | 0.0387156 |
| 17121970 | LINC00664\|CTD-2561J22.3 | −2.004541 | 0.0322094 |
| 17065663 | RNU6-729P | −1.956199 | 0.0217837 |
| 17028547 | N/A | −1.928579 | 0.0368662 |
| 17022610 | RNU6-957P | −1.806642 | 0.0058692 |
| 17035441 | AIF1 | −1.764652 | 0.046604 |
| 16825196 | NSMCE1 | −1.748448 | 0.0133459 |
| 16946689 | N/A | −1.717220 | 0.0396127 |
| 16906788 | N/A | −1.699501 | 0.0291432 |
| 16700250 | RNA5SP18 | −1.694822 | 0.0168599 |
| 17048704 | N/A | −1.658283 | 0.0448572 |
| 16729023 | RN7SKP297 | −1.632516 | 0.0112055 |
| 16938761 | RNU7-110P | −1.628371 | 0.0162458 |
| 16885703 | RNU6-127P | −1.622457 | 0.0155342 |
| 17000077 | N/A | −1.613790 | 0.0157459 |
| 16917881 | RP3-322G13.7 | −1.603191 | 0.0087606 |
| 16809811 | ZNF280D\|LOC145783 | −1.595119 | 0.0199623 |
| 16684087 | RNU6-949P | −1.568986 | 0.0107361 |
| 17092402 | N/A | −1.566978 | 0.0080698 |
| 16826158 | RNU6-845P | −1.557608 | 0.0081773 |
| 17038957 | RNF39 | −1.535992 | 0.0343131 |
| 16684995 | MIR552 | −1.523399 | 0.0241625 |
| 17103991 | RNA5SP505 | −1.522007 | 0.0133556 |
| 16897399 | RNU6-282P | −1.521112 | 6.44E−04 |
| 16696918 | N/A | −1.513779 | 0.014188 |

TABLE 2

Groups of genes the expression of which is increased in cell groups with high differentiation efficiency

| Unique Sorted Transcript ClusterID | gene symbol | Fold Change | p-value |
| --- | --- | --- | --- |
| 16788743 | MIR376B | 2.832859 | 0.02972 |
| 16788693 | SNORD114-26\|SNHG24\|RP11-909M7.3 | 2.504945 | 0.0459839 |
| 16788572 | N/A | 2.125842 | 0.0285273 |
| 17118804 | N/A | 2.041507 | 0.0058746 |
| 16662749 | N/A | 2.016646 | 0.0150649 |
| 17100659 | MT-TD | 1.913205 | 0.0101128 |
| 16747661 | MIR200C | 1.870588 | 0.0037729 |
| 17083911 | N/A | 1.804882 | 0.0280926 |
| 16788727 | MIR329-2 | 1.775661 | 0.0407001 |
| 16692589 | RNVU1-19 | 1.752449 | 0.0336053 |
| 16729321 | N/A | 1.732673 | 0.003036 |
| 16976012 | N/A | 1.731236 | 0.0048502 |
| 16697219 | RNA5SP72 | 1.685144 | 0.0466543 |
| 16798158 | SNORD116-11 | 1.631003 | 0.0415549 |
| 16990845 | N/A | 1.603721 | 0.0486904 |
| 17118850 | SNORA32\|TAF1D\|SNORA8\|SNORA1\|SNORA18\|SNORA40\|SNORD5\|MIR1304 | 1.581220 | 0.0359955 |
| 16830980 | N/A | 1.576090 | 0.0390183 |
| 16778675 | N/A | 1.571084 | 0.0067426 |
| 17110283 | RNU6-630P | 1.561571 | 0.0381138 |
| 16851422 | N/A | 1.561310 | 0.0360739 |
| 16797049 | N/A | 1.553732 | 0.0023054 |
| 16838105 | RNU6-227P | 1.551962 | 0.0274719 |
| 16831379 | RNA5SP436 | 1.548276 | 0.0018423 |
| 16875952 | VN1R1 | 1.547082 | 0.0499617 |
| 17117410 | LOC101929787 | 1.543222 | 0.0173222 |
| 17103230 | SPACA5\|SPACA5B | 1.526189 | 0.0017992 |
| 16999147 | DTWD2 | 1.521716 | 0.0387959 |
| 16688792 | RNA5SP22 | 1.520058 | 0.0009344 |
| 16718764 | MIR3663 | 1.512264 | 0.0347484 |
| 17072022 | N/A | 1.507210 | 0.008222 |
| 16679331 | N/A | 1.505864 | 0.0187971 |

Figure 5:
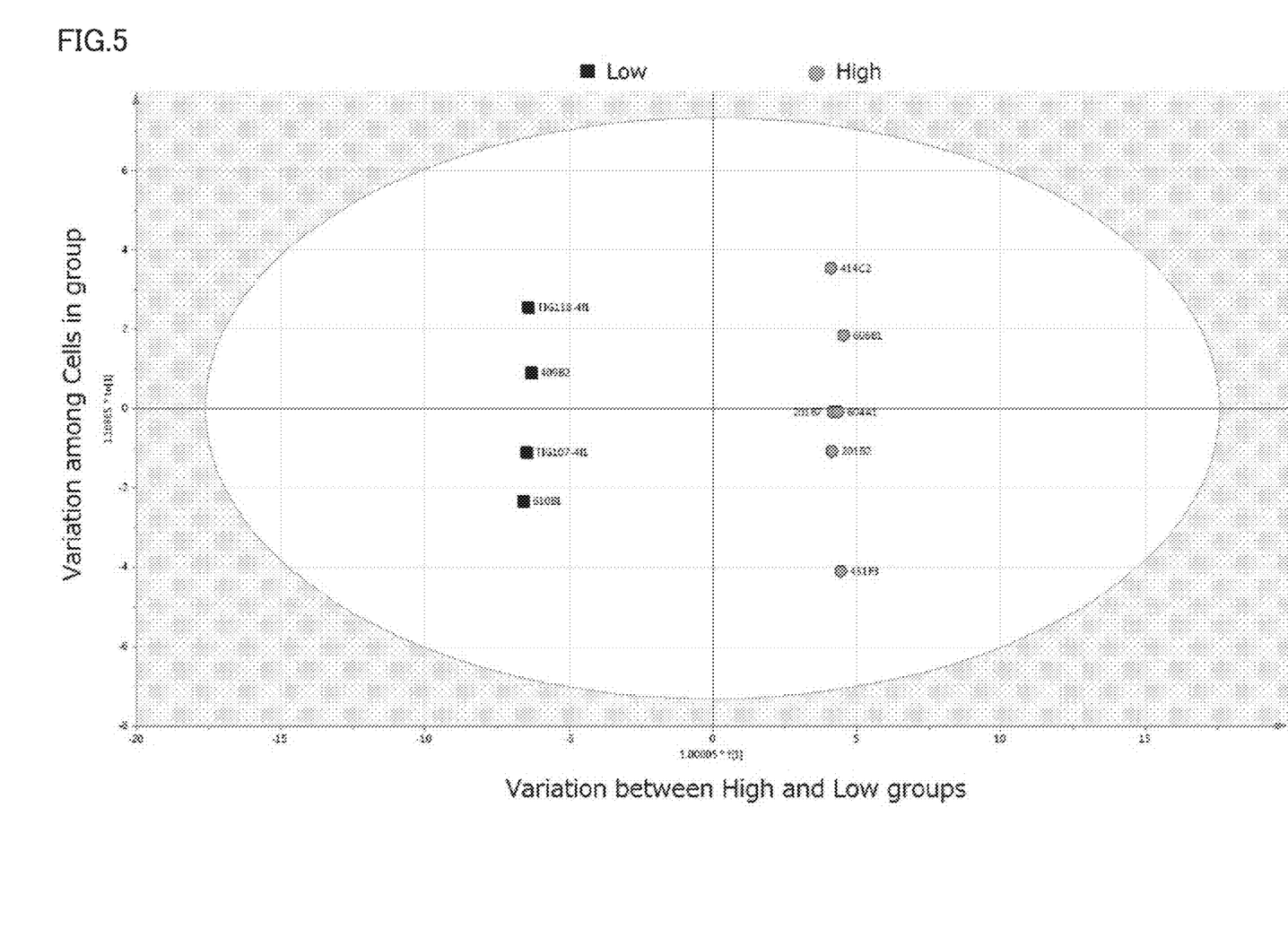
FIG. 5 shows iPS cell discrimination based on gene expression profiles.

Then, multivariate analysis (SIMCA13, manufactured by Umetrics) was performed by OPLS (orthogonal partial least square) using the gene expression profiles of the 61 genes and, thereby, a model that clearly discriminated between groups with high differentiation efficiency into NC cells and groups with low differentiation efficiency into NC cells (discrimination model) was constructed (FIG. 5). FIG. 5 shows iPS cell discrimination based on the gene expression profiles, with the abscissa representing variation between groups (High and Low cell groups in the drawing) and the ordinate representing variation among cells in a group. In FIG. 5, the cell groups with high differentiation efficiency into NC cells (High; •) and the cell groups with low differentiation efficiency into NC cells (Low; ■) are separated by a large margin in an axial direction and are discriminated clearly from each other.

Figure 6:
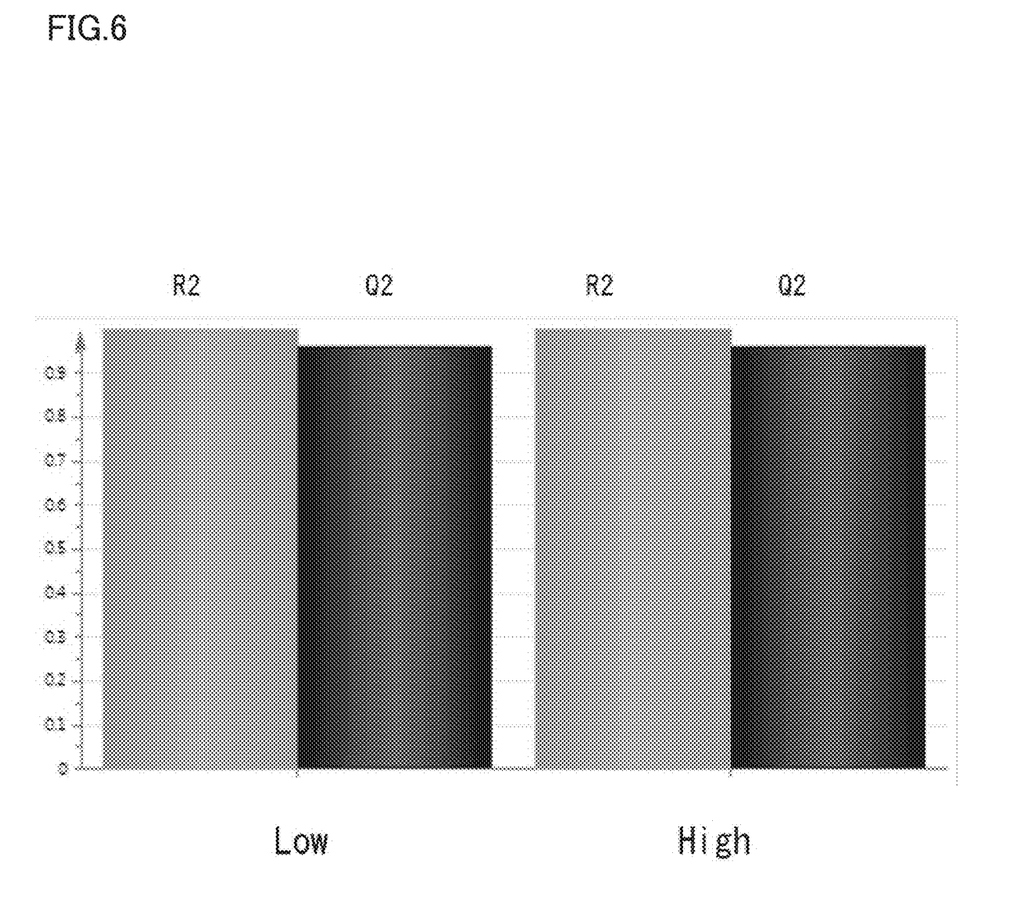
FIG. 6 shows evaluation of a discrimination model in terms of its compatibility with each of the cell groups with low differentiation efficiency into neural crest cells (NC cells) (Low) and the cell groups with high differentiation efficiency into neural crest cells (NC cells) (High).

Furthermore, fitness of the discrimination model to data (explanatory power, R2) and prediction reliability of fitness for an unknown sample (data) checked by cross-validation analysis (predictive power, Q2) were both high (FIG. 6). FIG. 6 shows evaluation of the discrimination model in terms of its compatibility with each of the cell groups with low differentiation efficiency into NC cells (Low) and the cell groups with high differentiation efficiency into NC cells (High). The ordinate represents R2 and Q2.

Figure 7:
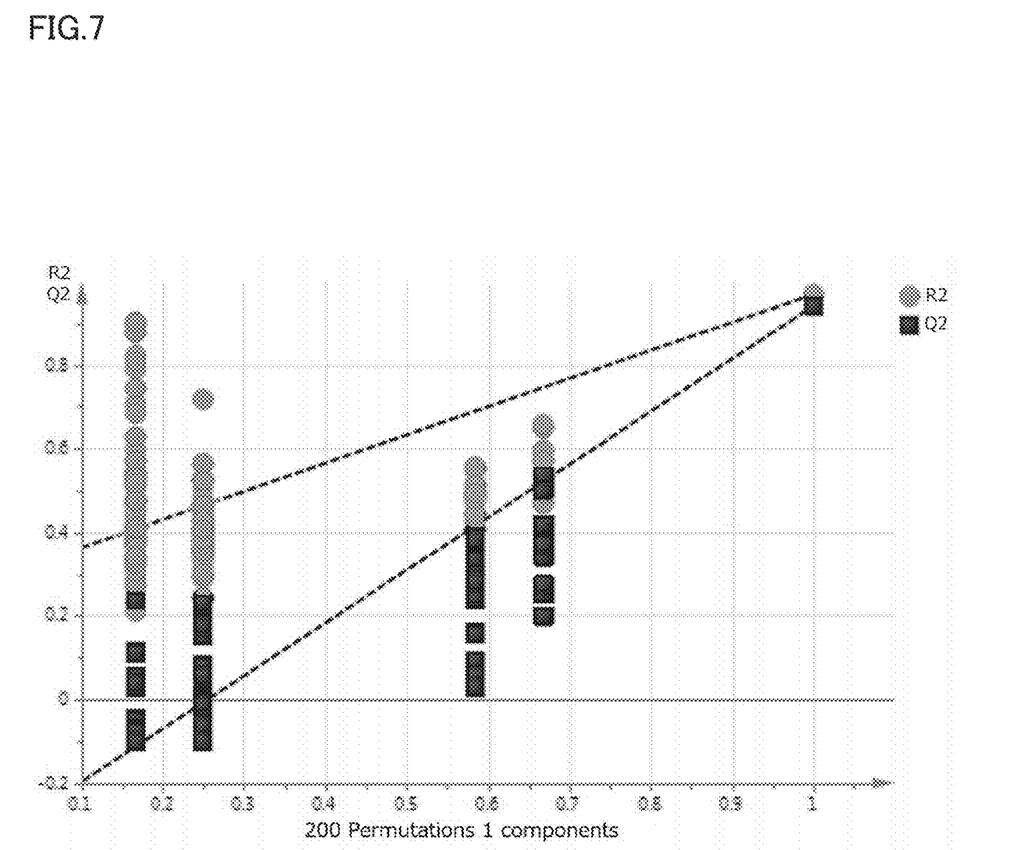
FIG. 7 shows results of data permutation validation (Permutation test).

Furthermore, validation of the discrimination model was performed by a data permutation test (Permutation test) and, as a result, the y intercept of the Q2 linear line was negative. This meant that the model did not overfit the original data alone (FIG. 7). FIG. 7 shows results of the data permutation validation (Permutation test), with the abscissa (the x axis) representing the frequency of data permutation in place of the original data (200 Permutations 1 components) and the ordinate (y axis) representing R2 or Q2. R2 and Q2 for x=1 are the values in original data. A smaller x corresponds to a greater frequency of data permutation.

Thus, a highly reliable discrimination-evaluation model for iPS cells can be constructed based on gene expression data.

Figure 8:
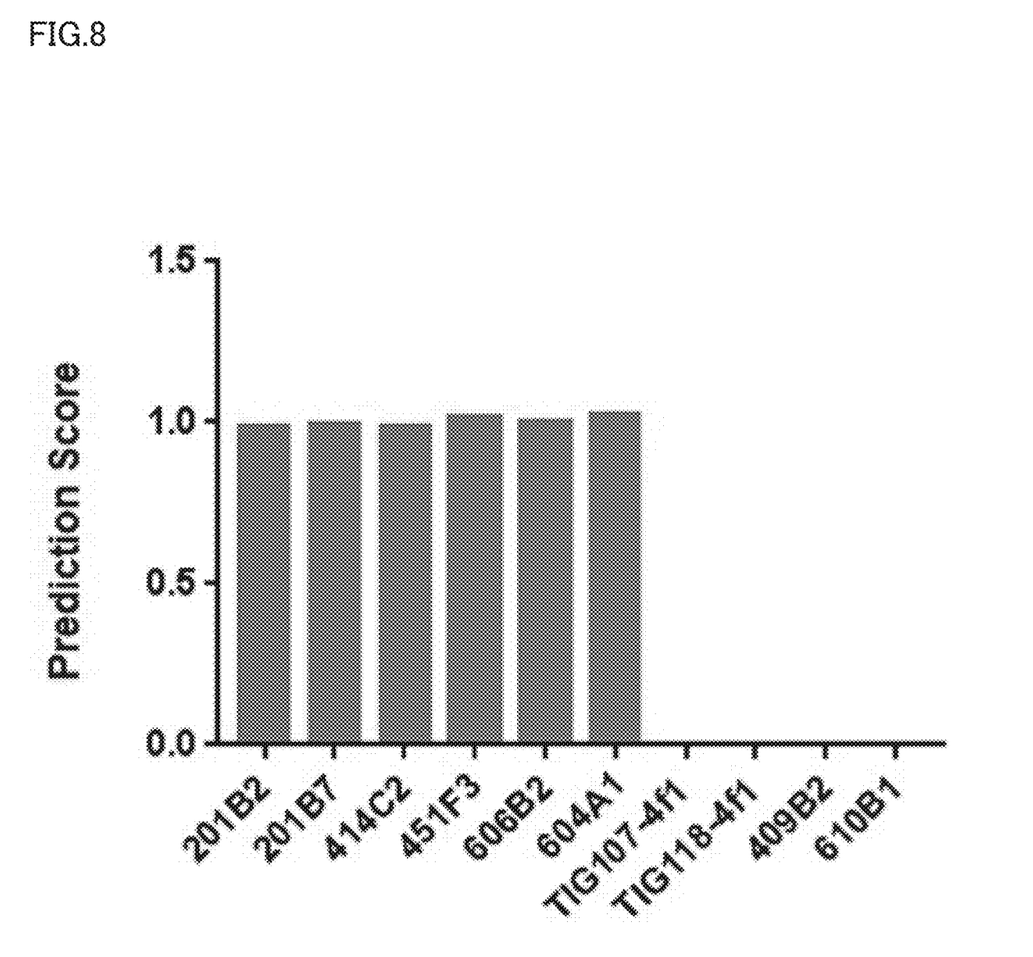
FIG. 8 shows differentiation potential prediction scores acquired based on gene expression profiles. When a higher prediction score is obtained, it is predicted that the iPS cells have a higher efficiency to generate CD271$^{high+}$ NC cells.

Furthermore, based on the discrimination model thus constructed and gene expression profiles of 61 genes for each iPS cell line, scoring of differentiation efficiency prediction was performed. The scoring showed a clear difference between cell lines with high differentiation efficiency and cell lines with low differentiation efficiency (FIG. 8). FIG. 8 shows differentiation potential prediction scores acquired based on the gene expression profiles, with the ordinate representing prediction score (Prediction Score). When a higher prediction score is obtained, a higher differentiation potential (a differentiation efficiency equal to or higher than 20%, for example) is predicted.

As describe above, the present invention is a method of predicting differentiation potential of undifferentiated iPS cells into cartilage cells based on gene expression data of the undifferentiated iPS cells.

The present invention is also a method of predicting differentiation potential of undifferentiated iPS cells into cartilage cells by predicting differentiation potential of the iPS cells into neural crest cells (NC cells) based on gene expression data of the undifferentiated iPS cells.

The undifferentiated iPS cells may be feeder-free undifferentiated iPS cells. The undifferentiated iPS cells are in an undifferentiated state, prior to differentiation into neural crest cells (NC cells).

The gene with decreased expression as the particular gene may be at least one selected from the group consisting of genes with gene IDs (Unique Sorted Transcript Cluster IDs) 16713399, 16984394, 17121974, 17122170, 16860191, 16999432, 17121970, 17065663, 17028547, 17022610, 17035441, 16825196, 16946689, 16906788, 16700250, 17048704, 16729023, 16938761, 16885703, 17000077, 16917881, 16809811, 16684087, 17092402, 16826158, 17038957, 16684995, 17103991, 16897399, and 16696918, and the gene with increased expression as the particular gene may be at least one selected from the group consisting of genes with gene IDs 16788743, 16788693, 16788572, 17118804, 16662749, 17100659, 16747661, 17083911, 16788727, 16692589, 16729321, 16976012, 16697219, 16798158, 16990845, 17118850, 16830980, 16778675, 17110283, 16851422, 16797049, 16838105, 16831379, 16875952, 17117410, 17103230, 16999147, 16688792, 16718764, 17072022, and 16679331.

More specifically, according to the present invention, gene expression profile data of target undifferentiated iPS cells is obtained and an expression level of a particular gene is obtained, an expression level ratio which is a ratio of the expression level of the particular gene to an expression level of the same gene in reference undifferentiated iPS cells with low differentiation potential (control) is calculated:

[Expression level ratio]=[Expression level of the particular gene in target undifferentiated iPS cells]/[Expression level of the same gene in reference undifferentiated iPS cells with low differentiation potential (control)], and when the expression level ratio thus calculated is lower than 0.9 for a gene with decreased expression or higher than 1.1 for a gene with increased expression, determination is made that the target undifferentiated iPS cells have a high differentiation potential into cartilage cells. The value thus used as a criterion for the determination may be selected as appropriate by a person skilled in the art. For instance, determination that the target undifferentiated iPS cells have a high differentiation potential into cartilage cells may be made when the expression level ratio thus calculated is lower than 0.8, lower than 0.7, or lower than 0.6 for a gene with decreased expression; and determination that the target undifferentiated iPS cells have a high differentiation potential into cartilage cells may be made when the expression level ratio thus calculated is higher than 1.2, higher than 1.3, or higher than 1.5 for a gene with increased expression.

Determination of differentiation potential of iPS cells may be made by obtaining gene expression profile data of target undifferentiated iPS cells, obtaining an expression level of a gene set selected as appropriate by a person skilled in the art, constructing a discrimination model by performing multivariate analysis by OPLS in the above-described manner, and calculating a prediction score from the model. The criterion of the determination may be selected as appropriate by a person skilled in the art; for instance, it may be selected by calculating the average of prediction scores calculated for undifferentiated iPS cells with low differentiation potential (control) and then, for example, using the value of [Average+2×(standard deviation)] as the criterion.

The reference undifferentiated iPS cells with low differentiation potential (control) may be selected as appropriate by a person skilled in the art. As an example of the undifferentiated iPS cells with low differentiation potential (control), the present specification teaches, in an earlier paragraph or earlier paragraphs, cell groups with low differentiation efficiency into NC cells (409B2, 610B1, TIG118-4f1, TIG107-4f1) after averaged. Other than these four cell lines, any cell line of undifferentiated iPS cells with low differentiation efficiency into NC cells of this type may be used as a control.

Techniques to induce differentiation of undifferentiated iPS cells into neural crest cells (NC cells) and techniques to induce differentiation of neural crest cells (NC cells) into cartilage progenitor cells and further into cartilage cells are known. See Japanese Patent Laying-Open No. 2016-88909, for example.

For instance, iPS cells are cultured on Matrigel (manufactured by Becton Dickinson) in mTeSR medium (manufactured by Stem-Cell Technologies) for nine days. On Day 9, culture was performed for six days in a first medium designed for induced differentiation into NC cells. The cells were then recovered with 0.05% trypsin-EDTA and replated on a fibronectin-coated dish, and this passage procedure is repeated every three days, three times in total, to induce differentiation into cartilage progenitor cells. The resulting cells are cultured in a medium supplemented with growth factors PDGF-BB, TGFβ3, and BMP4 designed for induced differentiation into cartilage, and thereby cartilage cells are obtained.

EXAMPLES

In the following, a specific description will be given of the present invention referring to examples. However, the present invention is not limited to these examples.

Experiment Example 1

In this example, ten undifferentiated iPS cell lines (201B2, 201B7, 414C2, 409B2, TIG118-4f1, 604A1, 606A1, 610B1, 451F3, TIG107-4f1) derived from human somatic cells were used.

The iPS cells derived from human somatic cells cultured on feeder cells (on-feeder) were replated on a culture dish coated with Matrigel (Matrigel Growth Factor Reduced manufactured by Corning) (subcultivation ratio, 1:5) and cultured in a feeder-free medium (mTeSR1 manufactured by VERITAS) for one week.

One week later, medium removal and PBS rinsing were performed and, to the cultured cells, 1 mL of RNA extraction buffer (RLT buffer (manufactured by QIAGEN)+5% mercaptoethanol) was added for RNA recovery. cRNA and ssDNA (single-strand cDNA) were synthesized from the extracted RNA and fragmented with uracil DNA glycosylase and apurinic/apyrimidinic endonuclease 1. Then, the fragmented ssDNA was biotin labeled, followed by hybridization with GeneChip® Human Gene 2.0 ST Array (manufactured by Thermo Fisher SCIENTIFIC) for 17 hours. After rinsing and staining, fluorescence was captured with a scanner and thereby gene expression data was obtained.

From the resulting expression data, the expression levels of the genes listed in Tables 1 and 2 were extracted, which were applied to a discrimination model (algorithm). Thereby, differentiation efficiency prediction scores were calculated (FIG. 8). When a higher prediction score is obtained, it is predicted that the iPS cells have a higher efficiency (differentiation potential) to generate $CD271^{high+}$ NC cells.

Experiment Example 2

This example checked versatility of the differentiation potential evaluation algorithm for use with undifferentiated iPS cells based on gene expression profiles.

Ten undifferentiated iPS cell lines (201B6, 253G4, 404C2, 454E2, 585A1, 585B1, 604A3, 604B1, 606A1, 610A2) derived from human somatic cells were used.

The iPS cells derived from human somatic cells cultured on feeder cells (on-feeder) were replated on a culture dish coated with Matrigel (Matrigel Growth Factor Reduced manufactured by Corning) (subcultivation ratio, 1:5) and cultured in a feeder-free medium (mTeSR1 manufactured by VERITAS) for one week.

One week later, medium removal and PBS rinsing were performed and, to the cultured cells, 1 mL of RNA extraction buffer (RLT buffer (manufactured by QIAGEN)+5% mercaptoethanol) was added for RNA recovery. cRNA and ssDNA (single-strand cDNA) were synthesized using the extracted RNA and fragmented with uracil DNA glycosylase and apurinic/apyrimidinic endonuclease 1. Then, the fragmented ssDNA was biotin labeled, followed by hybridization with GeneChip® Human Gene 2.0 ST Array (manufactured by Thermo Fisher SCIENTIFIC) for 17 hours. After rinsing and staining, fluorescence was captured with a scanner and thereby gene expression profile data was obtained.

Figure 9:
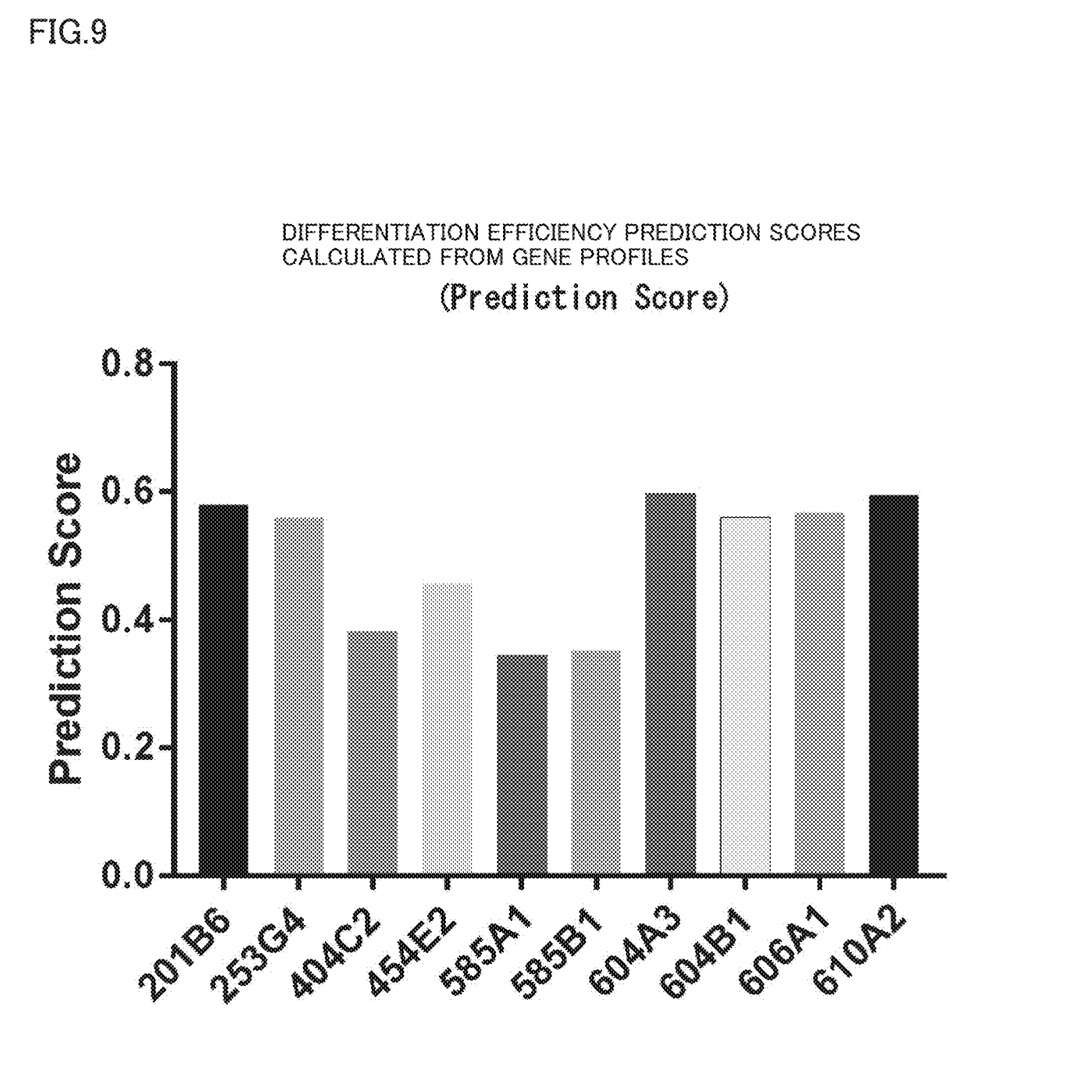
FIG. 9 shows differentiation potential prediction scores acquired based on gene expression profiles in Experiment Example 2.

The resulting gene profile data and a cell evaluation algorithm were used to calculate differentiation efficiency prediction scores (Prediction Score) (FIG. 9). FIG. 9 shows differentiation potential prediction scores acquired based on gene expression profiles, with the ordinate representing prediction score (Prediction Score).

Figure 10:
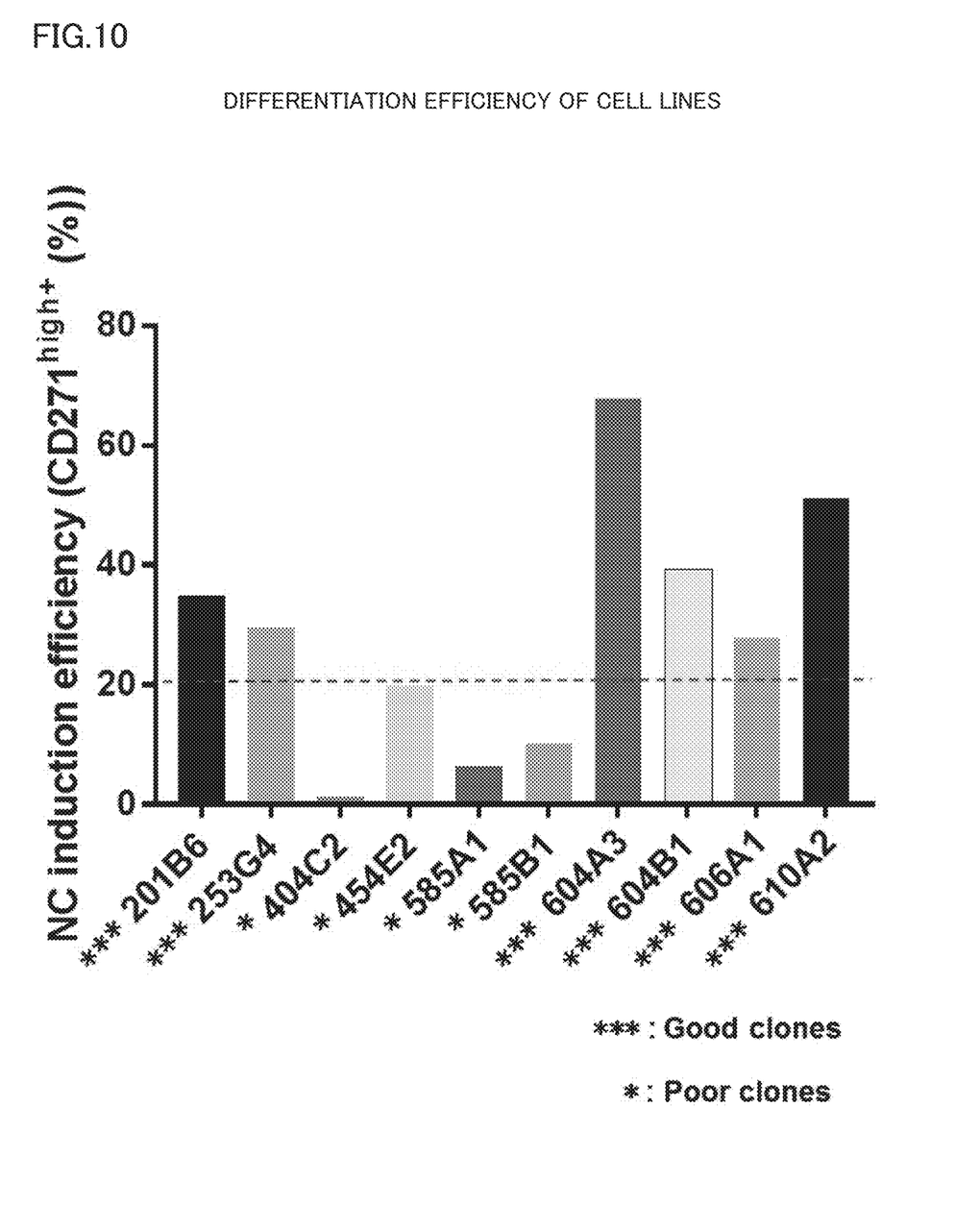
FIG. 10 shows differentiation efficiency of iPS cell lines into neural crest cells (NC cells) [NC induction efficiency (CD271$^{high+}$ (%))] in Experiment Example 2.

In the meantime, the undifferentiated iPS cell lines were induced to differentiate into neural crest cells (NC cells). Analysis by fluorescence flow cytometry (FACS) was performed to obtain the proportion of NC cells with high p75 expression in the NC cells thus induced differentiation. The proportion of $CD271^{high+}$ NC cells was calculated for use as NC differentiation efficiency. p75 is a low-affinity nerve growth factor receptor. FIG. 10 shows differentiation efficiency of iPS cell lines into NC cells [NC induction efficiency ($CD271^{high+}$ (%))]. The ordinate represents the proportion of $CD271^{high+}$ NC cells in the total NC cells. As shown in FIG. 10, the cells were divided into iPS cell groups with high differentiation efficiency into NC cells (Good clones; six cell lines 201B6, 253G4, 604A3, 604B1, 606A1, 610A2) and iPS cell groups with low differentiation efficiency into NC cells (Poor clones; four cell lines 404C2, 454E2, 585A1, 585B1). A proportion of $CD271^{high+}$ NC cells in the total NC cells equal to or higher than 20% was defined as high differentiation efficiency into NC cells.

Figure 11:
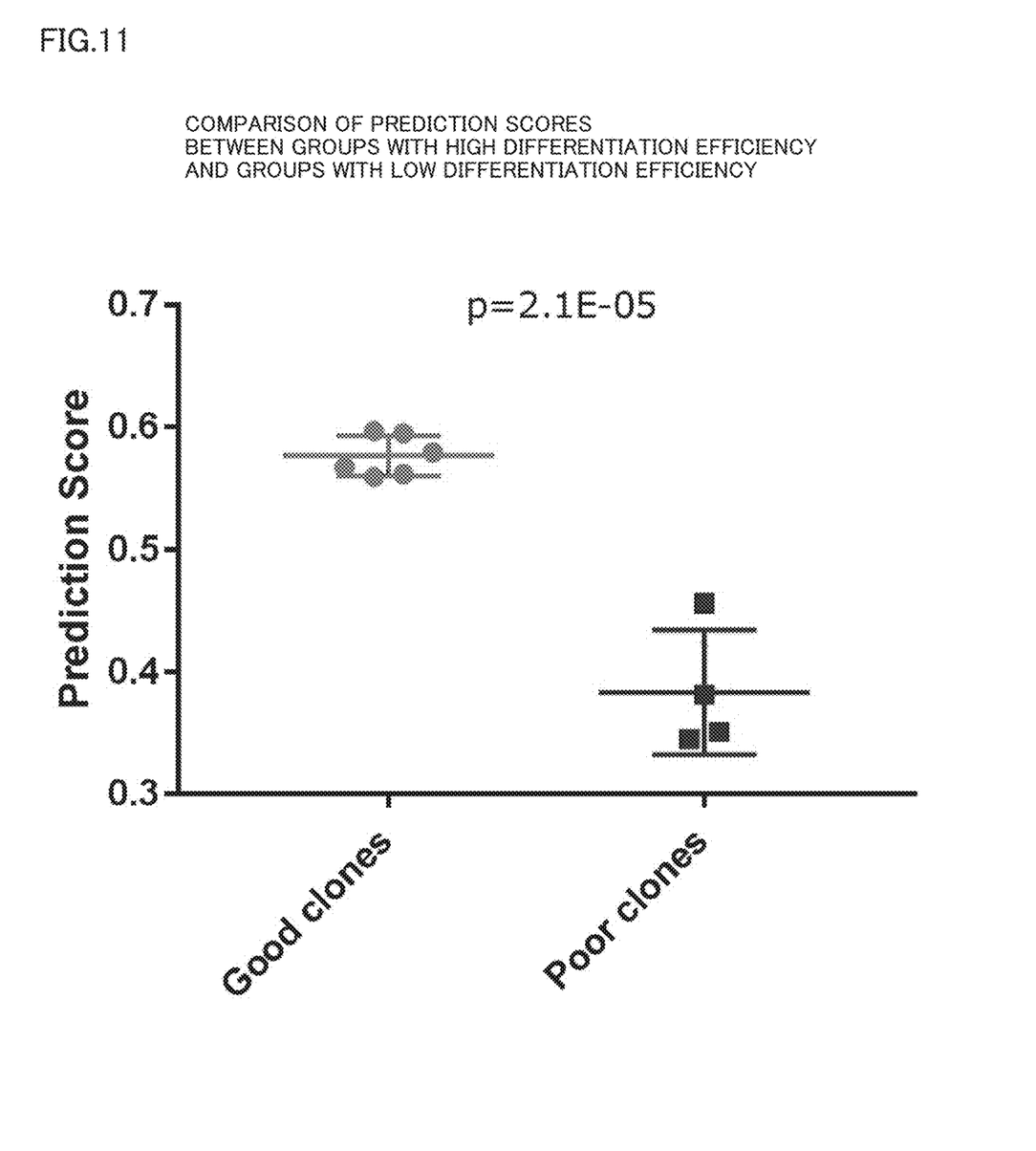
FIG. 11 shows comparison between prediction scores for iPS cell groups with high differentiation efficiency (Good clones) and prediction scores for iPS cell groups with low differentiation efficiency (Poor clones) in Experiment Example 2.

Among the resulting prediction scores for the ten iPS cell lines, comparison was made between iPS cell groups with high differentiation efficiency into NC cells (Good clones) and iPS cell groups with low differentiation efficiency into NC cells (Poor clones). The comparison revealed a significant increase in prediction score for the groups with high differentiation efficiency (Good clones) (FIG. 11). p=2.1E-05 (namely, $p=2.1\times10^{-5}$). FIG. 11 shows comparison between the prediction scores (Prediction Score) for the iPS cell groups with high differentiation efficiency (Good clones) and the prediction scores for the iPS cell groups with low differentiation efficiency (Poor clones).

Figure 12:
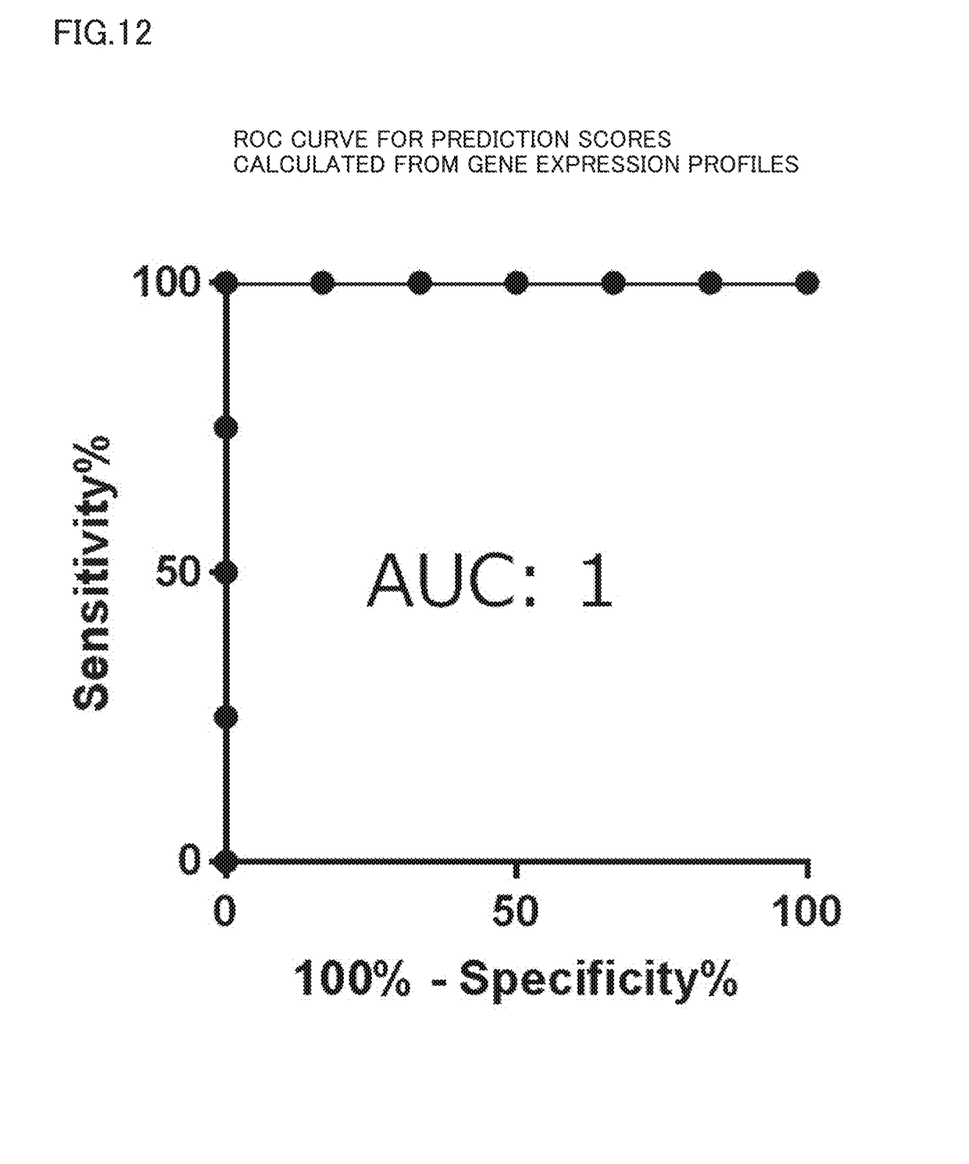
FIG. 12 is an ROC curve for prediction scores calculated from gene expression profiles in Experiment Example 2, with the abscissa representing 100-specificity (%) and the ordinate representing sensitivity (%).

The prediction scores calculated from the evaluation algorithm were used to draw an ROC curve (Receiver operation characteristic curve), and the area under curve (AUC) representing discrimination performance was 1. This shows that discrimination of undifferentiated iPS cells with unknown differentiation efficiency may be achieved by using the evaluation algorithm according to the present invention (FIG. 12). FIG. 12 is an ROC curve for prediction scores calculated from gene expression profiles, with the abscissa representing 100-specificity (%) and the ordinate representing sensitivity (%).

As discussed above, it is possible to predict differentiation potential of undifferentiated iPS cells based on the gene expression profiles according to the present invention.

The invention claimed is:

1. A method of differentiating undifferentiated iPS cells into cartilage cells, comprising:
    obtaining gene expression level data of a first set of genes and a second set of genes from target undifferentiated iPS cells,
    calculating an expression level ratio for each of the genes included in the first set and the second set, wherein:
    [Expression level ratio]=[Expression level of a gene from the target undifferentiated iPS cells]/[Control Expression level of the same gene from reference undifferentiated iPS cells with low differentiation potential],
    determining, based on the calculated expression level ratios, that the target undifferentiated iPS cells have a high differentiation potential into cartilage cells, and
    differentiating the target undifferentiated iPS cells that are determined to have a high differentiation potential into cartilage cells, wherein
    the first set of genes comprises genes with gene IDs 16713399, 16984394, 17121974, 17122170, 16860191, 16999432, 17121970, 17065663, 17028547, 17022610, 17035441, 16825196, 16946689, 16906788, 16700250, 17048704, 16729023, 16938761, 16885703, 17000077, 16917881, 16809811, 16684087, 17092402, 16826158, 17038957, 16684995, 17103991, 16897399, and 16696918, and
    the second set of genes comprises genes with gene IDs 16788743, 16788693, 16788572, 17118804, 16662749, 17100659, 16747661, 17083911, 16788727, 16692589, 16729321, 16976012, 16697219, 16798158, 16990845, 17118850, 16830980, 16778675, 17110283, 16851422, 16797049, 16838105, 16831379, 16875952, 17117410, 17103230, 16999147, 16688792, 16718764, 17072022, and 16679331.

2. The method according to claim 1, wherein the differentiation potential of the target undifferentiated iPS cells into cartilage cells is detected by predicting differentiation potential of the target undifferentiated iPS cells into neural crest cells (NC cells) based on gene expression data of the target undifferentiated iPS cells.

3. The method according to claim 1, wherein
    the determining further comprises:
    constructing a discrimination model,
    calculating a prediction score from the discrimination model and the gene expression level data, and
    using the prediction score for the detecting.

4. The method according to claim 1, wherein the target undifferentiated iPS cells are feeder-free undifferentiated iPS cells.

5. The method of claim 1, wherein the differentiating comprises culturing the target undifferentiated iPS cells in PDGF-BB.

6. The method of claim 1, wherein the differentiating comprises culturing the target undifferentiated iPS cells in TGFβ3.

7. The method of claim 1, wherein the differentiating comprises culturing the target undifferentiated iPS cells in BMP4.

8. The method of claim 1, wherein an expression level ratio lower than 0.9 from the first set indicates a high differentiation potential.

9. The method of claim 1, wherein an expression level ratio higher than 1.1 from the second set indicate a high differentiation potential.

* * * * *